United States Patent [19]
Wilson et al.

[11] Patent Number: 5,503,167
[45] Date of Patent: Apr. 2, 1996

[54] DEFORMABLE FACE SHIELD WITH MOUTHPIECE

[75] Inventors: Dorothy E. Wilson; James W. Wilson, both of 9351 SW. 23rd St. #3303, Fort Lauderdale, Fla. 33324

[73] Assignees: James W. Wilson; Dorothy E. Wilson, Ft. Lauderdale, Fla.

[21] Appl. No.: 179,423

[22] Filed: Jan. 10, 1994

[51] Int. Cl.⁶ ............................ A45D 40/30
[52] U.S. Cl. ............................ 132/319; 128/857
[58] Field of Search .................. 128/857, 858, 128/863, 201.26, 203.11, 206.29; 2/9, 174, 206; 132/319

[56] References Cited

U.S. PATENT DOCUMENTS

| | | | |
|---|---|---|---|
| 439,093 | 10/1890 | Barian | 128/206.29 |
| 596,919 | 1/1898 | Steves | 128/206.29 |
| 960,520 | 6/1910 | Dysthe | 128/863 |
| 1,199,529 | 9/1916 | Collman | 128/863 |
| 1,362,766 | 12/1920 | McGargill | 128/206.29 |
| 1,475,105 | 11/1923 | Aasen | 128/863 |
| 1,731,700 | 10/1929 | Battenfeld | 128/201.26 |
| 1,949,013 | 12/1932 | Gilchrist | 2/174 |
| 2,027,392 | 1/1936 | Manson | 128/206.29 |
| 3,015,105 | 1/1962 | Rogowski | 2/9 |
| 3,103,667 | 9/1963 | Rogowski | 2/9 |
| 3,152,588 | 10/1964 | Rogowski | 128/206.12 |
| 3,602,913 | 9/1971 | Neese | 2/9 |
| 3,705,760 | 12/1972 | Langendorfer et al. | 351/44 |
| 3,828,366 | 8/1974 | Conrad et al. | 2/174 |
| 3,963,034 | 6/1976 | Runberg et al. | 132/212 |
| 4,038,979 | 8/1977 | McCosker | 128/206.12 |
| 4,040,127 | 8/1977 | Slovitt et al. | 2/174 |
| 4,157,090 | 6/1979 | Phillips | 128/207.11 |
| 4,296,746 | 10/1981 | Mason, Jr. et al. | 128/201.15 |
| 4,411,023 | 10/1983 | Pinson | 128/201.26 |
| 4,856,535 | 8/1989 | Forbes | 128/857 |
| 4,872,465 | 10/1989 | Kuntz et al. | 128/857 |
| 4,873,972 | 10/1989 | Magidson et al. | 128/206.12 |
| 4,890,609 | 1/1990 | Wilson, II | 128/206.29 |
| 5,088,114 | 2/1992 | Salce et al. | 2/9 |
| 5,088,485 | 2/1992 | Schock | 128/206.29 |
| 5,243,708 | 9/1993 | Vanuch | 2/206 |
| 5,243,711 | 9/1993 | Graham | 2/439 |

*Primary Examiner*—Aaron J. Lewis
*Attorney, Agent, or Firm*—Malin, Haley, DiMaggio & Crosby

[57] ABSTRACT

A transparent, flexible and deformable face shield that adaptably fits and conforms to the contours of the wearer's face to protect the wearer's eyes, contact lenses, face, etc. from hairspray products or other products containing contaminants. The face shield includes an inwardly projecting mouthpiece which is gripped between the wearer's teeth to hold the shield in sealing engagement over the wearer's face, leaving both of the wearer's hands free to perform hairstyling or other functions.

13 Claims, 2 Drawing Sheets

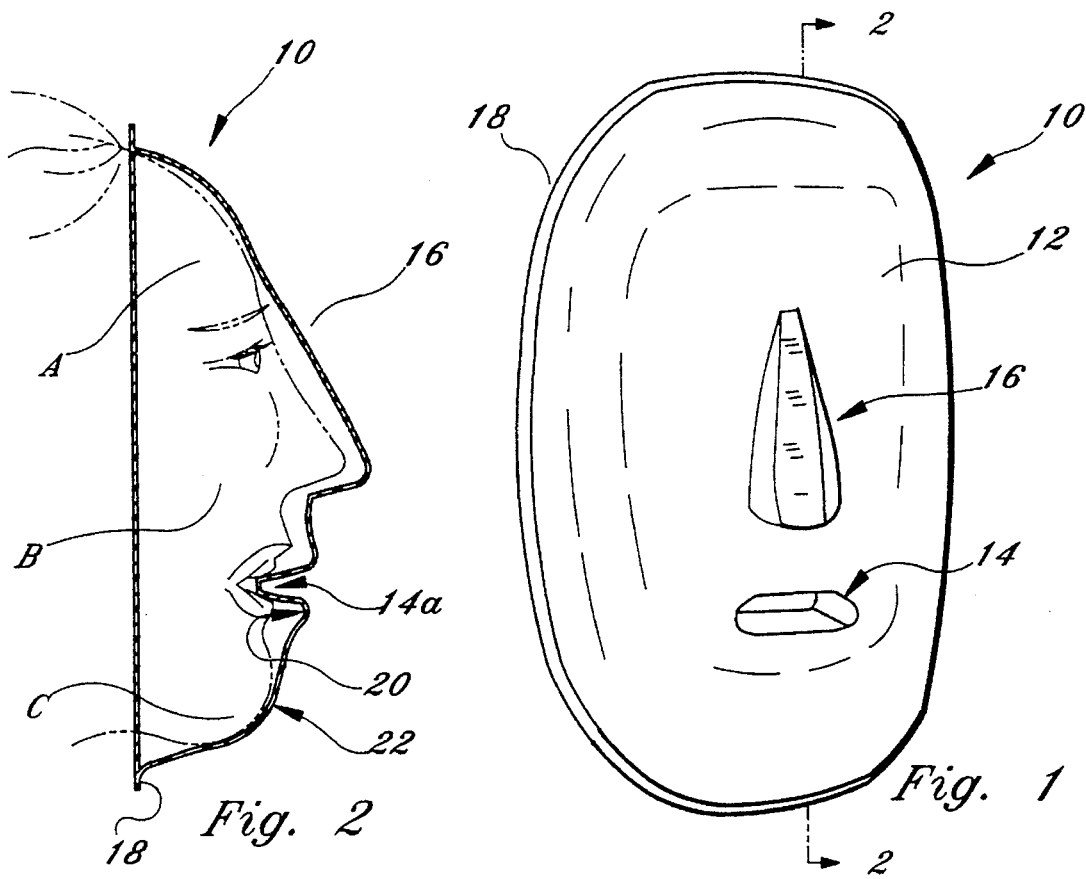
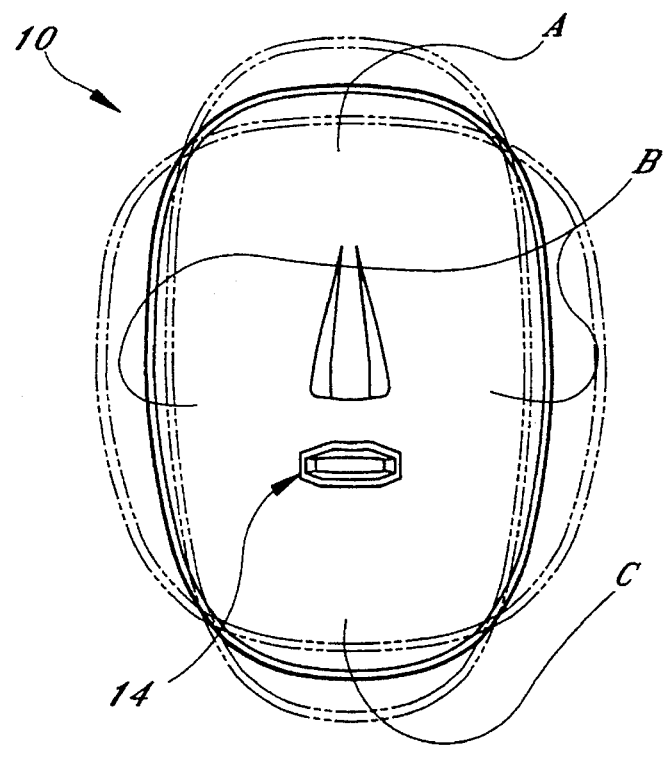

DEFORMABLE FACE SHIELD WITH MOUTHPIECE

BACKGROUND OF THE INVENTION

1. Field of the Invention

The instant invention is directed to a device adapted to cover and protect a wearer's face and respiratory tract from airborne hairstyling products, contaminants or the like. Specifically, the invention is directed to a deformable face shield having a mouthpiece for holding the shield in sealing engagement over the wearer's face without requiring the wearer to hold the shield in place. The shield protects the wearer's eyes, face and respiratory tract from hairspray products or other airborne matter without inhibiting the wearer's ability to style his or her hair using one or both hands or to perform other tasks requiring the use of one or both of the wearer's hands.

2. Description of the Background Art

It is undisputed and widely recognized that hairstyling products, such as hairspray, are harmful to the eyes and damaging to contact lenses. Documented research reveals that direct exposure of hairspray to the eye can result in keratitis, an inflammation of the cornea of the eye. Further, hairspray clogs the pores of permeable contact lenses, interfering with the oxygen supply to the cornea, which can result in corneal ulcers and blurred vision. Hairspray contaminates contact lenses and causes them to become "sticky" or "tacky", preventing them from moving freely on the wearer's eye, resulting in dryness and irritation to the cornea. Consequently, hairspray products contain warning labels such as ". . . do not spray in the eyes . . . " or ". . . do not use near the eyes . . . " Since it is virtually impossible to use hair spray without spraying in or around the eyes, eye care professionals recommend that hairspray users close their eyes while spraying. It is also advised that contact lenses not be inserted until hairspray use is completed.

Previously, the only protective devices available for hairstyling were either hand-held shields or goggles. Not surprisingly, these devices interfere with the hairstyling process. Hand-held shields do not provide a snug, contoured fit on the wearer's face, and they cannot be conveniently used since hairstyling usually requires the wearer to use both hands. Goggles and other conventional face protecting shields employ bands or cords, or they require earpieces, that extend into the hairline. These conventional devices are inconvenient since they interfere with the wearer's hair styling. In addition, these devices do not easily conform to a wide variety of face shapes and sizes, nor do they provide a snug fit to protect the wearer's eyes, face and respiratory tract. Although some attempts have been made to alleviate the above-noted problems, none have met with success or widespread approval.

Neese (U.S. Pat. No. 3,602,913) discloses an apparatus to protect the wearer's face from hairspray. Specifically, the reference discloses a one-piece molded mask with protective eye openings, a chin portion and a handle for holding the mask in place using one hand. The eyes are left exposed through the eye opening and the mask is opaque, making it difficult for the user to see what he or she is doing. In order to prevent hairspray from entering through the eye openings, the user must be extremely careful not to spray in or around the eye openings. Neese also discloses an embodiment without a handle, having inward-projecting tabs grasped in the mouth of the wearer. However, the tabs do not allow the wearer to control, nor do they have an effect on, the contour and fit of the mask against the face. In fact, the mask is rigid and cannot conform to various face shapes and sizes.

Another face shield is disclosed by Rogowski in U.S. Pat. No. 3,015,105. Rogowski '105 discloses a semi-rigid, form-fitting safety mask for shielding a person's face during beauty treatments or industrial tasks. This safety mask provides a channel for receiving the wearer's nose, the channel defining a passage for air. Earpieces are provided for holding the mask on the wearer's face. Rogowski's mask is semi-rigid, and it therefore cannot be easily adapted to fit all size faces.

It is apparent from the background art that there is still a need for a transparent shield that is conformable to a wide variety of faces and which can be worn without inhibiting the wearer's ability to style their own hair. The present invention solves these problems by providing a transparent, flexible shield having a mouthpiece by which the shield is securely and sealingly held against the wearer's face.

SUMMARY OF THE INVENTION

It is an object of the present invention to provide a flexible, deformable face shield having a mouthpiece which is used to hold the shield in place on the wearer's face.

It is another object of the invention to provide a transparent face shield that allows the wearer to see clearly while performing various functions.

It is also an object of this invention to provide a flexible, deformable face shield that conforms to a wide variety of face shapes and sizes and that sealingly engages the face.

It is still another object of the invention to provide a face shield with an open mouthpiece and a filter for filtering out pollutants, irritants or the like.

In accordance with these and other objects, the present invention comprises a flexible and deformable face mask shield molded into a concave shell having an inwardly protruding mouthpiece or bite plate and an outwardly projecting nose channel, the shield functioning as a form-fitting mask. Inherent in the face shield design is a unique flexibility that allows it to adapt to the contours of various face shapes and sizes. The shield may be deformed along at least three axes to achieve a snug fit around the brow and cheek areas of the face. The resilient characteristic or "memory" of the face shield allows it to return to its original shape when not being used. A plastic material such as vinyl, acrylic or other synthetic resin is used in manufacturing the shield so that it is transparent yet flexible and deformable. The inwardly protruding mouthpiece or bite plate may be formed integrally with the body of the shield, or as a separate piece, and this mouthpiece is used to hold the shield in place on the face when the wearer bites down on it, leaving the wearer's hands free for hairstyling or other activities. Since the shield is deformable and the mouthpiece is integral with, or attached to, the shield, a snug fit can be achieved by adjusting the position of the shield and biting down on the mouthpiece so that a tight seal is formed between the periphery of the shield and the wearer's face. With the shield in place, hairstyling products may be applied without contacting the wearer's eyes or face. The shield may also be worn while performing other tasks where protection of the face is necessary or desirable. Since the mask is preferably transparent, the wearer has full visibility.

In an alternate embodiment, the mouthpiece is provided with a breathing opening to the exterior of the shield and includes a filter for filtering inhaled air. In the alternative, a simple unfiltered air passage may be provided in the mouthpiece to allow the wearer to breathe through the shield. If commercial use is desired, the face shield may be formed from two pieces, the first piece comprising the face shield itself, and the second piece comprising a removable bite plate or bite plate cover which can be washed and/or sterilized.

BRIEF DESCRIPTION OF THE DRAWINGS

The invention is described in detail below with reference to the accompanying drawings, in which:

FIG. 1 is a perspective view of the preferred embodiment of the face shield of the invention;

FIG. 2 is a cross-sectional view of the face shield taken along line 2—2 of FIG. 1;

FIG. 3 is a plan view of the face shield in various stretched (deformed) and unstretched (non-deformed) positions;

DESCRIPTION OF THE PREFERRED EMBODIMENTS

Figure 4:
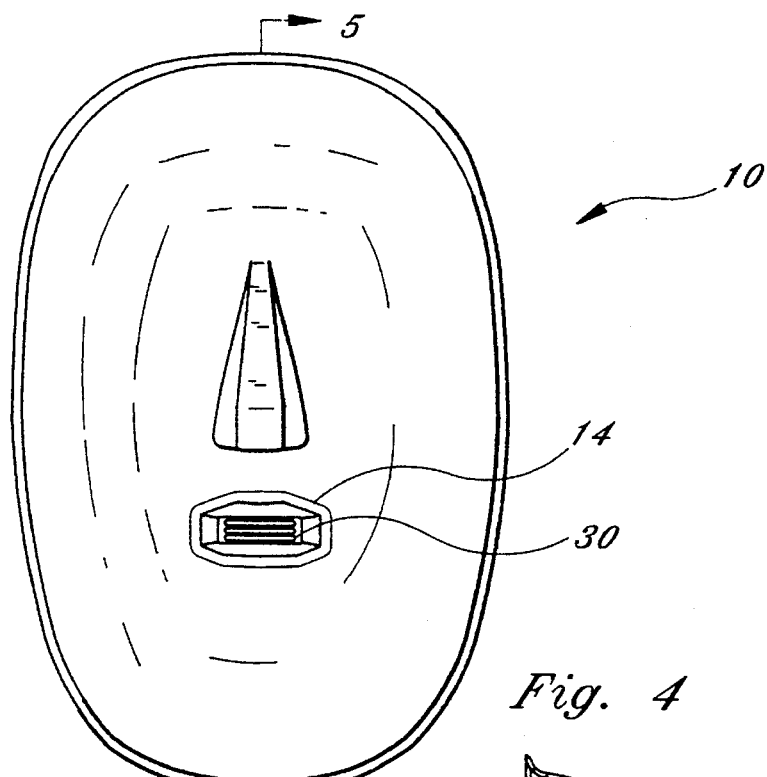
FIG. 4 is a perspective view of the face shield showing another embodiment having an air passageway without a filter.
Figure 5:
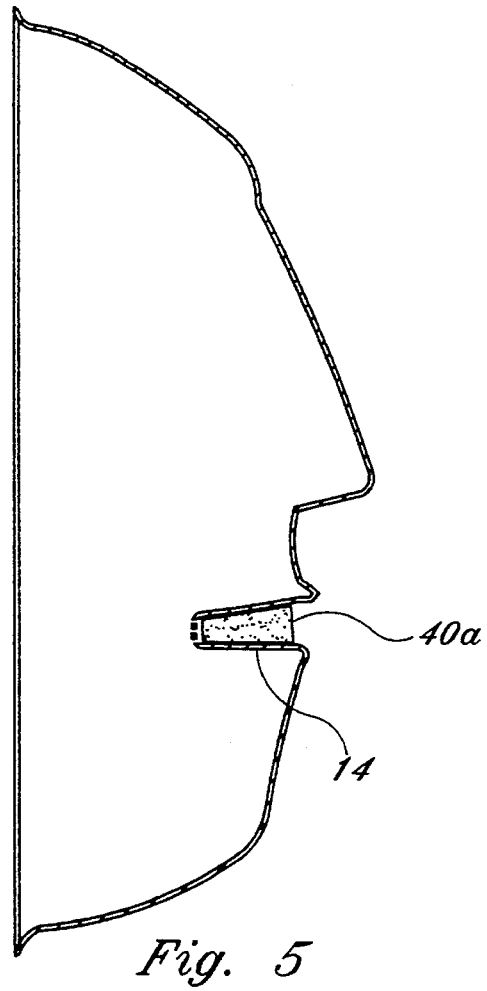
FIG. 5 is a cross-sectional view of the face shield taken along line 5—5 of FIG. 4 with a filter in the mouth cavity.

FIGS. 1–7 show a face shield 10 having a face-fitting contour for protecting the wearer's eyes, contact lenses and face from airborne contaminants, such as hairspray. The shield 10 comprises a body 12, a separate or integrally formed mouthpiece 14 and a nose channel 16. The shield is manufactured or molded into a single concave shape having an outer edge defined by a lip 18, which may be manufactured to lie in a single plane as shown in FIGS. 2 and 5. Lip 18 extends all of the way around the periphery of mask 10. The body 12 of the face shield 10 is flexible along at least three planes (see FIG. 3) so that it can be made to conform to the contours of different faces, providing a suitable seal in all cases. The mouthpiece 14 protrudes inwardly from the interior surface 20 and is received in the wearer's mouth when the shield 10 is held against the wearer's face. As shown in FIG. 2, the mouthpiece 14 is tapered in cross-section and forms a cavity 14a which enhances the deformability and flexibility of face shield 10 when drawn into the mouth and allows the wearer to bite down and "fix" the shield in a form-fitting position over the wearer's face. The mouthpiece 14 may be any cross sectional shape without departing from the spirit and scope of the instant invention. Nose channel 16 is integrally formed with the face shield 10, and projects outwardly from the exterior surface 22 of the body 12, providing clearance for the nose. Such clearance is necessary so that the shield fits snugly to the face around the wearer's eye and cheek areas.

The face shield 10 may be fabricated from a single piece of thermoplastic material such as vinyl, acrylic or other synthetic resin. It is light, flexible and easily deformable, giving the shield three dimensional flexibility as shown in FIG. 3 so that it fits snugly to the brow, cheek and chin areas of the wearer. The uniform structure of the face shield 10 further facilitates mass production of the shield. Since the posterior edge 18 is defined in one plane a single rule die can be used to cut the shield from carrier sheets. The shield 10 may also be made by vacuum forming, blow molding or injection molding of a clear plastic material or the like. In a vacuum forming process, the mask forming material is heated to a thermoplastic state and then placed over a three-dimensional mold. Since thermoplastic materials have a "memory" which causes them to return to their original state, the resiliency of the material allows the face shield to retain its utility over time.

In use, the face shield 10 is placed on, and pressed firmly against, the wearer's face so that the brow, cheek and chin areas are in firm contact with the shield (at points A, B, and C, respectively, as shown in FIG. 1 and 3). Additional pressure may be placed on the shield to cause the lateral cheek areas B to move inwardly causing the mouthpiece 14 to move further into the wearer's mouth. As this external pressure is exerted on the body 12, face shield 10 conforms more closely to the contours of the face until, finally, the shield 10 is engaged against the wearer's face, at which time the bite plate or mouthpiece 14 is pinched between the wearer's teeth so the shield is maintained in sealing engagement around the wearer's face.

The mask is also suitable for use in connection with emergency medical situations, carpentry and other activities where protection is desired. In addition, the shield may be worn to protect clothes from cosmetics which often stain or smudge the garments when they are pulled over the wearer's head.

Figure 6:
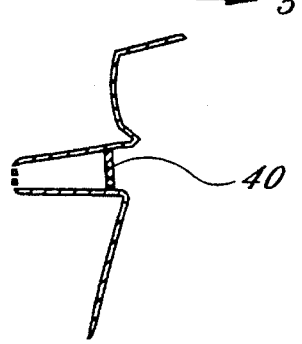
FIG. 6 is a cross-sectional view of the mouth cavity with a filter strip at the front.

In the embodiment shown in FIG. 4, the mouthpiece 14 includes an air passageway 30 to allow the wearer to breathe through the mouthpiece 14 while wearing the shield 10. Referring to FIG. 5, the filter 40 may comprise a removable foam filter insert 40a made of a permeable membrane to allow breathing. Alternatively, the filter 40 may be secured in front of the cavity 14a with the use of pressure sensitive adhesives or the like as seen in FIG. 6.

Figure 7:
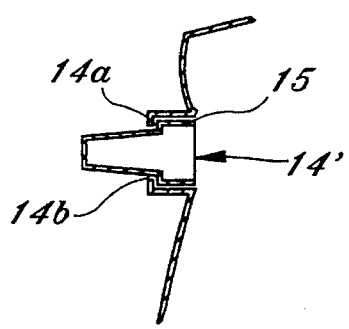
FIG. 7 is a cross-sectional view of the mouth cavity with a removable mouthpiece.

In an alternate embodiment, the mouthpiece may comprise a removable bite plate 14', shown in FIG. 7. The bite plate 14' mates with an aperture 14b defined by cavity 14a. A head 15 is formed at one end of the bite plate 14' which abuts the cavity 14a around the aperture 14b when inserted through the aperture 14b. The head 15 secures the mouthpiece in the cavity 14a and prevents it from passing completely through the aperture 14b.

The instant invention has been shown and described herein in what are considered to be the most practical and preferred embodiments. It is recognized, however, that reasonable departures may be made therefrom within the spirit and scope of the invention, and that obvious modifications will occur to those persons skilled in the art.

What is claimed is:

1. A face shield, comprising:

a transparent, generally concave, semi-rigid shell adapted to cover the entirety of a wearer's face, said shell defining interior and exterior surfaces and an outer peripheral lip lying in a single plane; and a mouth engaging member extending inwardly from the interior surface of said shell, said mouth engaging member adapted to be grasped between the wearer's teeth after the outer peripheral lip is pressed against the wearer's face, said mouth engaging member maintaining substantially all of the outer peripheral lip in engagement with the wearer's face.

2. The face shield as recited in claim 1, further comprising a face-contacting lip extending along at least a portion of a peripheral edge of said shell.

3. The face shield as recited in claim 1, wherein said face shield and said mouthpiece are integrally formed.

4. The face shield as recited in claim 1, wherein said face shield comprises a transparent thermoplastic.

5. The face shield as recited in claim 1, wherein said mouth engaging member comprises upper and lower sections projecting inwardly from the interior surface of said shell, said upper and lower sections being tapered, connected together at distal ends thereof to form a tapered mouthpiece.

6. The face shield as recited in claim 5, wherein said mouthpiece is integrally formed with said shell.

7. The face shield as recited in claim 5, further comprising an air passageway defined by said mouthpiece.

8. The face shield as recited in claim 7, further comprising a filter associated with the air passageway.

9. The face shield as recited in claim 8, wherein said filter comprises a permeable foam material.

10. The face shield as recited in claim 9, wherein said filter substantially fills the air passageway defined by said mouthpiece.

11. The face shield as recited in claim 1, wherein said mouth engaging member comprises upper and lower sections projecting inwardly from the interior surface of said shell, said upper and lower sections being connected together at distal ends thereof to form a substantially rectangular mouthpiece.

12. The face shield as recited in claim 1, wherein said mouth engaging member is detachable from said shell for cleaning and replacement.

13. The face shield as recited in claim 1, wherein said mouth engaging member comprises, in cross section, opposed inwardly projecting L-shaped walls and a corresponding tapered, removable, bite plate which at least partially surrounds said mouth engaging member.

\* \* \* \* \*